(12) United States Patent
Fickel et al.

(10) Patent No.: US 11,185,849 B2
(45) Date of Patent: Nov. 30, 2021

(54) NANO-SIZED ZEOLITE CATALYST HAVING A HIGH SILICA TO ALUMINA RATIO

(71) Applicant: SABIC Global Technologies, B.V., Bergen op Zoom (NL)

(72) Inventors: Dustin Fickel, Sugar Land, TX (US); Katherine Barton, Sugar Land, TX (US)

(73) Assignee: SABIC Global Technologies, B.V., Bergen op Zoom (NL)

( * ) Notice: Subject to any disclaimer, the term of this patent is extended or adjusted under 35 U.S.C. 154(b) by 0 days.

(21) Appl. No.: 16/497,949

(22) PCT Filed: Mar. 29, 2018

(86) PCT No.: PCT/US2018/025029
§ 371 (c)(1),
(2) Date: Sep. 26, 2019

(87) PCT Pub. No.: WO2018/187141
PCT Pub. Date: Oct. 11, 2018

(65) Prior Publication Data
US 2020/0023342 A1  Jan. 23, 2020

Related U.S. Application Data (60) Provisional application No. 62/481,444, filed on Apr. 4, 2017.

(51) Int. Cl.
*B01J 29/70* (2006.01)
*B01D 53/94* (2006.01)
*B01J 29/76* (2006.01)
*B01J 29/78* (2006.01)
*B01J 35/00* (2006.01)
*C01B 39/48* (2006.01)
*C07C 2/12* (2006.01)
*C07C 29/03* (2006.01)

(52) U.S. Cl.
CPC ...... *B01J 29/7015* (2013.01); *B01D 53/9418* (2013.01); *B01J 29/763* (2013.01); *B01J 29/783* (2013.01); *B01J 35/0013* (2013.01); *C01B 39/48* (2013.01); *C07C 2/12* (2013.01); *C07C 29/03* (2013.01); *B01D 2255/50* (2013.01); *B01D 2255/9202* (2013.01); *B01J 2229/186* (2013.01); *C01P 2004/03* (2013.01); *C07C 2529/76* (2013.01); *C07C 2529/78* (2013.01)

(58) Field of Classification Search
CPC ...... B01J 29/70; B01J 29/7015; B01J 29/763; B01J 29/783; B01J 38/0013; B01J 2229/186; B01D 53/9418; B01D 2255/50; B01D 2255/9202; C01B 39/48; C07C 2/12; C07C 29/03; C07C 2529/76; C07C 2529/78; C01P 2004/03
USPC ........................................................ 502/60
See application file for complete search history.

(56) References Cited

U.S. PATENT DOCUMENTS

2018/0186707 A1* 7/2018 Abudawoud ........... C07B 41/04

OTHER PUBLICATIONS

Deimund et al. ("Effect of Heteroatom Concentration in SSZ-13 on the Methanol-to-Olefins Reaction" ACS Catal. 2016, 6, 542-550) (Year: 2016).*

* cited by examiner

*Primary Examiner* — Edward M Johnson
(74) *Attorney, Agent, or Firm* — Sheri Higgins Law; Sheri Higgins (57) ABSTRACT

A catalyst includes a zeolite, wherein the zeolite has: a CHA framework; a particle size less than or equal to 100 nanometers; and a silica to alumina mole ratio in the range of about 50:1 to about 150:1. The catalyst can include a metal dopant. The catalyst can be used for purifying a product by flowing a reactant across the catalyst to form the product; and condensing or separating the product. The product can be an olefin or alkenes with an increased carbon chain. The catalyst can be used for selective catalytic reduction of nitrogen oxide or a gas to liquid reaction. A method of producing the catalyst can include selecting the concentration of a crystal growth inhibitor based on the ratio of the silica precursor and an alumina precursor such that the zeolite crystals have a mean particle size less than or equal to 100 nanometers.

15 Claims, 7 Drawing Sheets

NANO-SIZED ZEOLITE CATALYST HAVING A HIGH SILICA TO ALUMINA RATIO

TECHNICAL FIELD

The field concerns that use of nano-sized aluminosilicate zeolite SSZ-13 catalysts for the conversion of reactants into desired products.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION OF THE INVENTION

Zeolites are microporous, aluminosilicate minerals that can be useful as a catalyst in a variety of chemical reactions. As used herein, a "catalyst" means a material that alters the rate of a chemical reaction. Zeolites occur naturally or can be synthetically produced. Zeolites generally comprise silicon (Si), aluminum (Al), and oxygen (O), and can also include other elements, such as titanium (Ti), tin (Sn), zinc (Zn), and copper (Cu). Zeolites can be classified according to their structure. For example, a zeolite having a tetrahedral framework composed of double six-membered ring units, which connect to form a cavity with eight-membered ring pore windows can be classified as a zeolite with a chabazite (CHA) structure. One example of a synthetically produced CHA zeolite is SSZ-13. During synthesis of zeolite crystals, a structure directing agent (SDA) can be used to produce crystals with the desired structure.

SSZ-13 can be used as a catalyst in a variety of chemical reactions. For example, a SSZ-13 catalyst can be used to produce olefins from reactants of chloromethane or methanol. A SSZ-13 zeolite can also include other elements, such as copper. Cu-SSZ-13 catalysts can be used, for example, to produce alcohols from alkane reactants and provide selective catalytic reduction (SCR) to convert nitrogen oxides ($NO_x$) into diatomic nitrogen and water.

A SSZ-13 catalyst can play a crucial role in the production of other industrial products and in reducing environmental impacts. For example, ethylene (an olefin) is one of the largest organic chemical feedstocks by volume that can be used as an intermediary to produce polymers, such as polyethylene, and many other chemicals and products. Moreover, nitrogen oxides are a major atmospheric pollutant produced through the combustion of fossil fuels, for example, in diesel engines. Many negative environmental effects result from having nitrogen oxides in the atmosphere, including the greenhouse effect, acid rain, and ozone depletion.

Zeolites can be generally synthetically produced by slow crystallization of silica-alumina precursors, generally as a gel. The crystal structure and other properties of the zeolite can depend on the precursors, pH of the system, temperature, seeding time, and reaction time. The size of the crystals produced can play an important role in the zeolites' ability to function as a catalyst. For example, small or nano-sized crystals possess higher geometric surface area; and thus, the number of easily accessible zeolite cages near the surface is much higher compared to larger crystals. Moreover, these small or nano-sized crystals can also provide short diffusion path lengths through the crystal, which can be very important in many reactions the zeolite catalyst is employed. During the synthesis of zeolite crystals, a growth inhibitor can be included to produce crystals with a desired size.

Nano-sized SSZ-13 zeolite crystals have been successfully produced. These SSZ-13 zeolites typically have low molar silica ($SiO_2$) to alumina ($Al_2O_3$) ratios of less than 40:1 or 20:1. The ability to successfully produce these low molar ratio, nano-sized SSZ-13 zeolite crystals appears to depend on the concentration of the growth inhibitor used. However, there is a need and an on-going industry-wide concern to synthetically produce nano-sized SSZ-13 zeolites with a higher molar ratio of the silica to alumina precursors. Generally, an increase in the molar ratio increases the strength of the individual acid sites. Whereas, at lower molar ratios, even though there are more acid sites, their individual strengths are weaker.

It has been unexpectedly discovered that nano-sized, high molar ratio SSZ-13 zeolite crystals can be synthetically produced. The produced zeolite crystals can be used as a catalyst for a variety of chemical reactions. The zeolite crystals can also include other elements, such as copper, which can be useful in even other chemical reactions. Such chemical reactions include any reactions in which small or larger crystals are typically used—with the nano-sized crystals advantageously providing increased geometric surface area for reactants and shorter diffusion path lengths.

It is to be understood that the discussion of preferred embodiments regarding the catalyst is intended to apply to the composition and method embodiments.

According to certain embodiments, a catalyst comprises: a zeolite, wherein the zeolite has: a CHA framework; a particle size less than or equal to 100 nanometers; and a silica to alumina mole ratio in the range of about 50:1 to about 150:1.

According to certain embodiments, the zeolite is an aluminosilicate SSZ-13 zeolite having a chabazite (CHA) framework. As used herein, an "aluminosilicate zeolite" is a zeolite that does not include phosphorus atoms in the framework structure. SSZ-13 can be synthesized in the anhydrous state, in terms of mole ratios of oxides as follows: (0.5 to 1.0) $R_2O$: (0 to 0.50) $M_2O$—$W_2O_3$: (greater than 5) YO, wherein M is an alkali metal cation, W is selected from the group consisting of aluminum, gallium and mixtures thereof, Y is selected from the group consisting of silicon, germanium and mixtures thereof, and R is a quaternary lower alkylammonium cation compound.

The pore diameter of zeolite catalyst can range from about 3 angstroms (Å) to about 15 Å. For SSZ-13, the pore size is generally about 3.72 Å×3.72 Å. The pore volume of the zeolite catalyst can be about 0.29 milliliters per gram (ml/g).

The particle size of the zeolite is less than or equal to 100 nanometers (nm). According to certain other embodiments, the particle size of the zeolite is less than or equal to 50 nm. Generally, zeolite crystals are not uniform in shape. As such, the crystals can have varying dimensions, for example, cross-sectional lengths. As used herein, any reference to the "particle size" of the zeolite or zeolite crystals is the mean particle size of the crystals at the crystal(s) largest dimension. By way of example, a zeolite crystal can have a largest dimension of 80 nm with smaller dimensions of less than 80 nm. The "mean particle size" can include zeolite crystals falling above and below the mean.

The aluminosilicate zeolite catalyst can include other metals as dopants. Non-limiting examples of dopants include copper (Cu), nickel (Ni), iron (Fe), zinc (Zn), manganese (Mn), and molybdenum (Mo). The type of dopant selected can depend on the specific chemical reaction the catalyst will be used. For example, a Cu-SSZ-13 catalyst can be useful in producing alcohols from alkane reactants and selective catalytic reduction (SCR) of nitrogen oxides ($NO_x$). Dopants can be added to the catalyst using known dopant techniques, for example, impregnation, ion exchange, chemical deposition, etc. The concentration of the dopant can depend on the desired activity of the catalyst, among others. The concentration of the dopant can range from 0.00001 weight percent (wt. %) to 5 wt. %.

According to certain other embodiments, a method of producing a catalyst comprises: combining a silica precursor and an alumina precursor, wherein the ratio of the silica precursor to the alumina precursor is in the range of about 50:1 to about 150:1; adding a crystal growth inhibitor; adding a structure directing agent; and crystallizing the zeolite, wherein the zeolite crystals have a CHA framework and a mean particle size less than or equal to 100 nanometers.

The silica precursor and alumina precursor can include silica (including colloidal silica suspension in water), aluminum sulfate, aluminum sulfate octadecahydrate, aluminum hydroxide, or sodium aluminate. The method can further include the addition of other ingredients, such as sodium hydroxide, potassium hydroxide, and deionized water. The precursors, optional other ingredients, the crystal growth inhibitor, and the structure directing agent can be combined and heated at a desired temperature for a desired amount of time to crystallize the zeolite in a CHA type structure. The desired temperature can range from about 150° C. to about 170° C. The desired amount of time can range from about 3 days to about 6 days.

The structure directing agent can be any agent that produces a zeolite with the CHA framework. Suitable examples of a structure directing agent that produces a CHA zeolite include, without limitation, N,N,N-1-trimethyladamantammonium hydroxide, benzyltrimethyl ammonium hydroxide, choline chloride, N alkyl-3-quinuclidinol, N,N,N-tri-alkyl-1-adamantammonium, and N,N,N-trialkyléexoaminonorbornane, and combinations thereof. The structure directing agent can be in a concentration in the range of about 9 wt. % to about 18 wt. % of the solution.

The crystal growth inhibitor can be polyethyleneimine "PEI". A polymer is a large molecule composed of repeating units, typically connected by covalent chemical bonds. The number of repeating units of a polymer is referred to as the chain length of the polymer. A polymer has an average molecular weight, which is directly related to the average chain length of the polymer. The average molecular weight of a polymer has an impact on some of the physical characteristics of a polymer, for example, its solubility. For a copolymer, each of the monomers will be repeated a certain number of times (number of repeating units). The average molecular weight ($M_w$) for a copolymer can be expressed as follows:

$$M_w = \Sigma w_x M_x$$

where $w_x$ is the weight fraction of molecules whose weight is $M_x$. According to certain embodiments, the polyethyleneimine has a molecular weight in the range of about 1,000 to about 5,000.

According to certain embodiments, the crystal growth inhibitor (e.g., polyethyleneimine) is in a concentration in the range of about 0.1 to about 1.0 weight percent of the silica precursor and alumina precursor. According to certain other embodiments, the concentration of the crystal growth inhibitor is selected based on the ratio of the silica precursor and the alumina precursor such that the zeolite crystals have a mean particle size less than or equal to 100 nm. The concentration of the crystal growth inhibitor can also be selected based on the ratio of the silica precursor and the alumina precursor such that the zeolite crystals have a mean particle size less than or equal to 50 nm. It has unexpectedly been discovered that the concentration of the crystal growth inhibitor is less than was thought necessary for a SSZ-13 zeolite having a high silica to alumina molar ratio. Previous work showed higher concentrations of a crystal growth inhibitor was necessary for SSZ-13 zeolites with a low silica to alumina ratio. Therefore, it was believed that the same or similar concentrations of the crystal growth inhibitor would be applicable for high molar ratios. However, these concentrations did not produce nano-sized SSZ-13 crystals. As used herein, a "high silica to alumina molar ratio" means a ratio greater than 40:1. As used herein, a "low silica to alumina ratio" means a ratio of less than 40:1.

According to certain other embodiments, a method of purifying a product comprises: providing the zeolite catalyst; flowing a reactant across the catalyst to form the product; and condensing or separating the product.

According to certain embodiments, the catalyst is used for olefin production. The reactant can be selected from alkyl halides (e.g., chloromethane and bromomethane), alcohols (e.g., methanol), or alkyl amines (e.g., methyl amines). The product can be an olefin (e.g., ethylene, butylene, propylene, etc.). While the following discussion pertains to the use of an alkyl halide for olefin production, using the catalyst, it is to be understood that the embodiments are equally applicable to other reactants that can be used for olefin production.

The reactant can be flowed across the catalyst as a feed. An alkyl halide feed can include one or more alkyl halides. The alkyl halide feed can contain alkyl mono halides, alkyl dihalides, alkyl trihalides, preferably alkyl mono halide with less than 10% of other halides relative to the total halides. The alkyl halide feed can also include inert compounds, such as nitrogen, helium, and steam. The alkyl halide in the feed may have the following structure: $C_nH_{(2n+2)-m}X_m$, where n and m are integers, n ranges from 1 to 5, preferably 1 to 3, even more preferably 1, m ranges 1 to 3, preferably 1, and X is Br, F, I, or Cl. According to certain embodiments, the feed includes at least 50 wt. % of the alkyl halide under reaction conditions sufficient to produce an olefin hydrocarbon product comprising $C_2$-$C_4$ olefins. In other aspects the feed may include at least 75 wt. %, preferably at least 80 wt. %, and most preferably at least 90 wt. % of the alkyl halide. Non-limiting examples of alkyl halides include methyl chloride, methyl bromide, methyl fluoride, or methyl iodide, or any combination thereof. In preferred aspects, the methyl halide is chloromethane. The feed can include oxygenated compounds (e.g., alcohols). The oxygenated compounds can be methanol, ethanol, or combinations thereof.

The SSZ-13 catalyst catalyzes the conversion of alkyl halides to $C_2$-$C_4$ olefins. Reaction scheme (1) is an example of conversion of methyl chloride to ethylene, propylene, and butylene using the SSZ-13 catalyst.

(1)

where X is Br, F, I, or Cl. Besides the $C_2$-$C_4$ olefins the reaction may produce some byproducts such as methane, $C_5$ olefins, $C_2$-$C_5$ alkanes, and aromatic compounds such as benzene, toluene, and xylene. The produced byproducts can be separated from the olefin product stream and used in other downstream processes. For example, HCL can be generated from an alkyl halide. The HCl can be separated from the olefin product and provided to an oxyhydrochlorination unit. In an oxyhydrochlorination, the HCl can be reacted with methane and oxygen to produce chloromethane and water. The produced chloromethane can then be recycled back into the feed for the production of olefins.

Conditions sufficient for olefin production include temperature, time, alkyl halide concentration, space velocity, and pressure. The temperature range for olefin production may range from about 200° C. to about 600° C. or about 300° C. to about 500° C. A weight hourly space velocity (WHSV) of alkyl halide higher than 0.5 h$^{-1}$ can be used, preferably between 0.5 and 10 h$^{-1}$, more preferably between 0.5 and 5 h$^{-1}$, even more preferably between 0.5 to 3 h$^{-1}$. The conversion of alkyl halide to olefins can be performed at a pressure less than 1.4 MPa (200 psig) or atmospheric conditions. Typically the conditions for olefin production may be varied based on the type of the reactor. The method can further include collecting or storing the produced olefin hydrocarbon product along with using the produced olefin hydrocarbon product to produce a petrochemical or a polymer.

According to certain other embodiments, the catalyst can be used to produce alkenes with an increased carbon chain. By way of example, the reactant can be ethylene and the product can be propylene.

According to certain other embodiments, the catalyst further comprises a metal, such as copper. As such, the catalyst can be nano-sized Cu-SSZ-13. Although the following discussion pertains to Cu-SSZ-13, it is to be understood that other metals, such as iron or cobalt can be used instead of copper. The thermal stability of SSZ-13 is increased significantly when copper is exchanged into the aluminosilicate zeolite compared to the acid form of the zeolite, NH4/H+-SSZ-13. Cu-SSZ-13 is generally more thermally stable than other copper zeolites, such as Cu-ZSM-5.

According to certain embodiments, the Cu-SSZ-13 catalyst is used for selective catalytic reduction (SCR) or deNO$_x$ of nitrogen oxide (NO$_x$). According to this embodiment, the reactant is nitrogen oxide. The products can be nitrogen gas and water. The feed stream can include exhaust gas, for example, from diesel engines. The feed stream can also include a gaseous reductant, typically anhydrous ammonia, aqueous ammonia or urea that is added to a stream of flue or exhaust gas and is adsorbed onto the catalyst. Carbon dioxide (CO$_2$) can be a reaction product when urea is used as the reductant.

The NOx reduction reaction takes place as the gases pass through a catalyst chamber. Before entering the catalyst chamber the ammonia or other reductant (such as urea), is injected and mixed with the gases. The chemical equations for a stoichiometric reaction using either anhydrous or aqueous ammonia for a selective catalytic reduction process are shown below in reaction schemes (2)-(4), with several secondary reactions that can occur as shown in reaction schemes (5)-(7):

(2)

(3)

(4)

(5)

(6)

(7)

According to certain embodiments, the Cu-SSZ-13 catalyst is used in a gas to liquid (GTL) reaction. According to this embodiment, the reactant is an aliphatic hydrocarbon having a carbon chain in the range of $C_1$ to $C_6$. The product is an alcohol of the reactant. By way of example, the reactant can be methane (CH$_4$) and the product can be methanol. The methods can further include additional steps. For example, methane to methanol conversion can be performed in a stepwise fashion and consists of: (i) oxidation at high temperature (≥450° C.) of the Cu-SSZ-13 with O$_2$, (ii) contact of the Cu-SSZ-13 with methane at lower temperatures (120-200° C.), and (iii) admission of water, in either a liquid or gas phase.

The catalyst can have a desired activity. Catalytic activity can be measured by the amount of reactant (e.g., chloromethane, methane, and ethylene) converted and can be expressed as the % moles of the reactant converted with respect to the moles of reactant fed into the reaction system. According to certain embodiments, the catalyst has an activity of at least 70% or preferably an activity of at least 90% under operating conditions.

The catalyst can also have a desired selectivity of the desired products (e.g., olefins, alcohol, and nitrogen gas). According to certain embodiments, the catalyst has a selectivity of desired products of at least 60% or preferably at least 70% under operating conditions.

Figure 1:
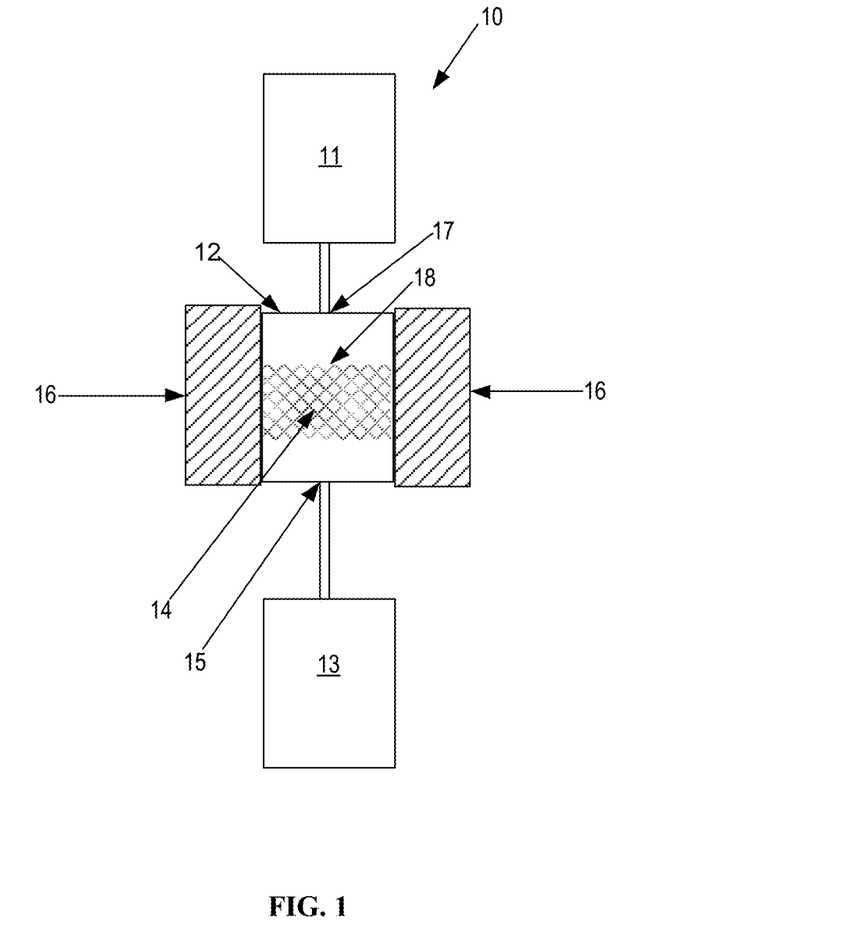
FIG. 1 is a schematic illustration of a system reactor for producing products from reactants using a nano-sized aluminosilicate catalyst.

Referring to FIG. 1, a reactor system 10 is illustrated, which can be used to convert reactants to products using the aluminosilicate catalyst. The system 10 can include a reactant feed 11, a reactor 12, and a collection device 13. The reactant feed 11 can be configured to be in fluid communication with the reactor 12 via an inlet 17 on the reactor. The reactant feed can be configured such that it regulates the amount of reactant entering the reactor 12. The reactant feed 11 can also include other fluids, such as carrier fluids. The reactor 12 can include a reaction zone 18 having the aluminosilicate zeolite catalyst 14. The amounts of the reactant feed 11 and the catalyst 14 used can be modified as desired to achieve a given amount of product produced by the system 10. Non-limiting examples of reactors that can be used include fixed-bed reactors, fluidized bed reactors, bubbling bed reactors, slurry reactors, rotating kiln reactors, or any combinations thereof when two or more reactors are used. In a commercial process, reactor 12 is a fluidized bed reactor with a catalyst regenerator unit. The reactor 12 can include an outlet for products produced in the reaction zone 18. The collection device 13 can be in fluid communication with the reactor 12 via the outlet 15. Both the inlet 17 and the outlet 15 can be open and closed as desired. The collection device 13 can be configured to store, further process (e.g., condense or separate), or transfer desired reaction products for other uses. The system 10 can also include a heating source 16. The heating source 16 can be configured to heat the reaction zone 18 to a desired operating temperature that is sufficient to convert the reactants from the reactant feed to products. A non-limiting example of a heating source 16 can be a temperature controlled furnace. Additionally, any unreacted reactant can be recycled back into the reactant feed to further maximize the overall conversion of reactant to products.

EXAMPLES

To facilitate a better understanding of the present invention, the following examples of certain aspects of preferred embodiments are given. The following examples are not the only examples that could be given according to the present invention and are not intended to limit the scope of the invention.

Aluminosilicate zeolites were prepared as follows: water was combined with a structure directing agent of N,N,N-trimethyl-1-adamantylammonium hydroxide (abbreviated "R" in the Tables) in a plastic beaker equipped with a magnetic stir bar. If a crystal growth inhibitor of polyethyleneimine "PEI" was used, it was added and stirred before adding the alumina source. To this solution, the alumina source was then added and stirred on a magnetic stir plate for 10-15 min. The silica source was then added while stirring, and the solution was allowed to age for 24 hr at room temperature. As an example, for a typical 35-mL synthesis with a composition of $100SiO_2:60R:4000H_2O:1Al_2O_3$, 0.31 g PEI and 9.627 g of deionized $H_2O$ were combined with 19.791 g of 25% N,N,N-trimethyl-1-adamantylammonium hydroxide. To this solution, 98% aluminum sulfate octadecahydrate and 5.861 g of LUDOX® AS-40, which is a 40 wt. % colloidal silica suspension in water. After aging, the solution was poured into high-pressure, Teflon-lined Parr reactors and crystallized at 150-170° C. in a tumbling synthesis oven for 4-6 days at a tumbling rate of approximately 35 rpm. After cooling to room temperature, the solutions were transferred to Falcon tubes and centrifuged for 30-60 min. The supernatant was then decanted, deionized water was added, and the solution was mixed and centrifuged again. This process was repeated three times, and the final supernatant was decanted. The isolated zeolite was then transferred to a ceramic calcination dish and dried at 90° C. overnight before calcining at 550° C. with a temperature rate of ramping of 3° C./hr for 7 hr in air. To prepare the catalyst for the reactor, the obtained powder from the calcination was pressed and sized to 20/40 standard mesh size.

Figure 2:
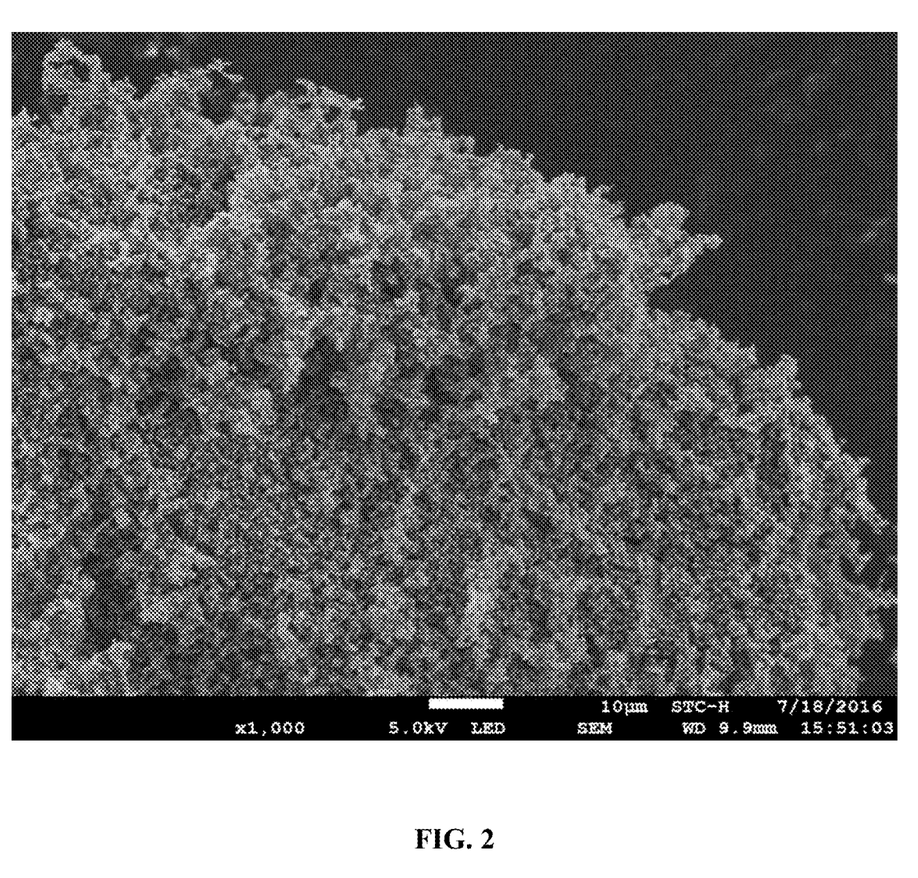
FIGS. 2-7 are scanning electron microscope "SEM" images of a variety of zeolites according to various embodiments, as discussed in the Examples section.
Figure 3:
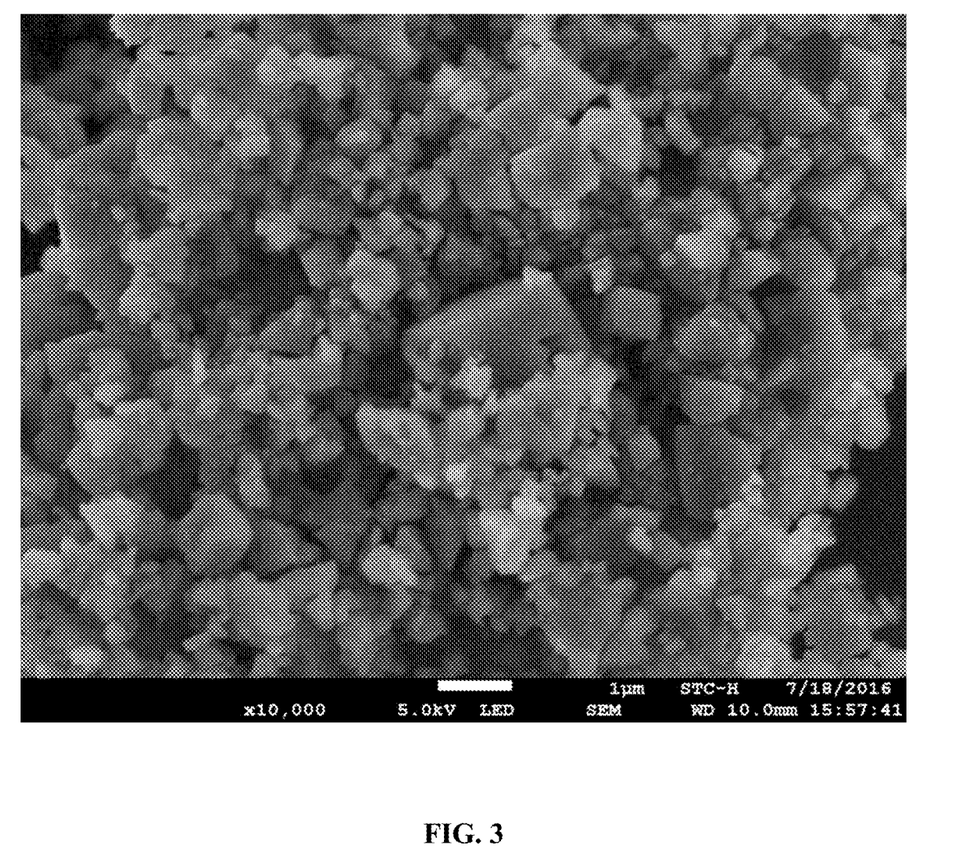
Figure 4:
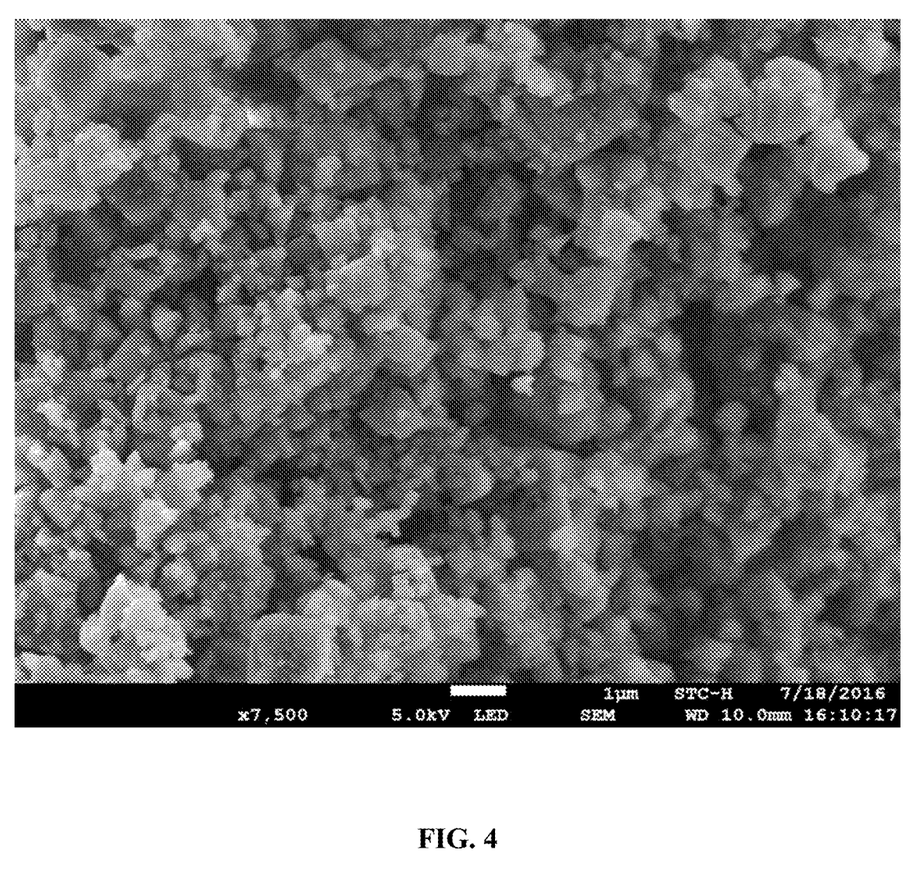

Table 1 shows the theoretical and actual molar ratios for the zeolite. The concentration of PEI was 0.31 wt. % by weight of the silica and alumina precursors. The crystallization temperature was 170° C. with a crystallization time of 5 days. As can be seen in FIGS. 2-4, the zeolite possessed good crystal structure and an average particle size of 100 nm.

TABLE 1

|  | Si/Al$_2$ ratio | Si | R | H$_2$O | Al$_2$ | PEI |
| --- | --- | --- | --- | --- | --- | --- |
| Theoretical | 100:1 | 100 | 60 | 4,000 | 1 | 0.22 |
| Actual | 99.8:1 | 99.8 | 59.8 | 4,008.7 | 1 | 0.22 |

Figure 5:
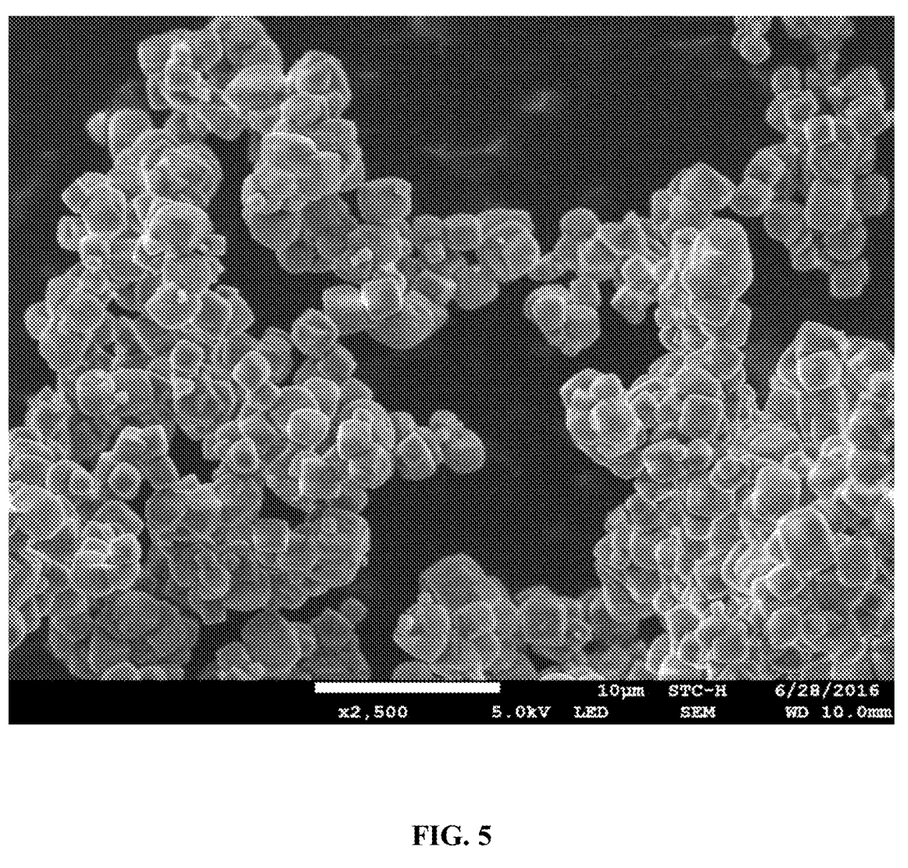

Table 2 shows the theoretical and actual molar ratios for the zeolite. No PEI was added to the silica and alumina precursors. The crystallization temperature was 170° C. with a crystallization time of 3 days. As can be seen in FIG. 5, the zeolite possessed good crystal structure and an average particle size of about 1,500 nm.

TABLE 2

|  | Si/Al$_2$ ratio | Si | R | H$_2$O | Al$_2$ |
| --- | --- | --- | --- | --- | --- |
| Theoretical | 100:1 | 100 | 80 | 4,230 | 1 |
| Actual | 100.6:1 | 100.6 | 80.5 | 4,273.5 | 1 |

Figure 6:
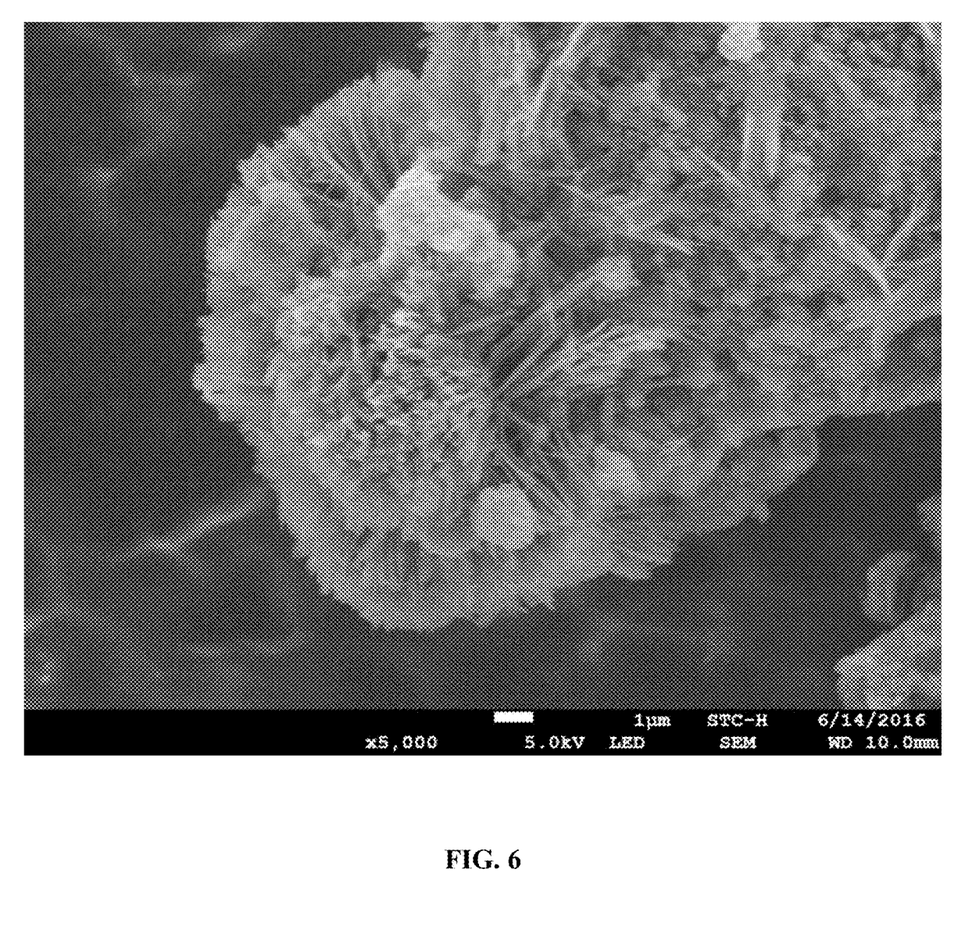

Table 3 shows the theoretical and actual molar ratios for the zeolite. The concentration of PEI was 1.5 wt. % by weight of the silica and alumina precursors. The crystallization temperature was 170° C. with a crystallization time of 3 days. As can be seen in FIG. 6, no zeolite was formed, as the resulting material was amorphous in structure. This indicates that with a silica to alumina ratio of 100:1, a PEI concentration of 1.5 wt. % was too high and did not form a zeolite (for example, when compared to FIGS. 2-4 with a PEI concentration of 0.31 wt. %). It has unexpectedly been discovered that the concentration of the crystal growth inhibitor is less than was thought necessary for a SSZ-13 zeolite having a high silica to alumina molar ratio. Previous work showed higher concentrations of a crystal growth inhibitor was necessary for SSZ-13 zeolites with a low silica to alumina ratio. Therefore, it was believed that the same or similar concentrations of the crystal growth inhibitor (e.g., concentrations ≥1.0 wt. %) would be applicable for high molar ratios. As shown, these higher concentrations did not produce a nano-sized zeolite, but rather, produced an amorphous material, which was unexpected.

TABLE 3

|  | Si/Al$_2$ ratio | Si | R | H$_2$O | Al$_2$ | PEI |
| --- | --- | --- | --- | --- | --- | --- |
| Theoretical | 100:1 | 100 | 80 | 3,500 | 1 | 0.88 |
| Actual | 100:1 | 99.4 | 79.6 | 3,428.0 | 1 | 0.88 |

Figure 7:
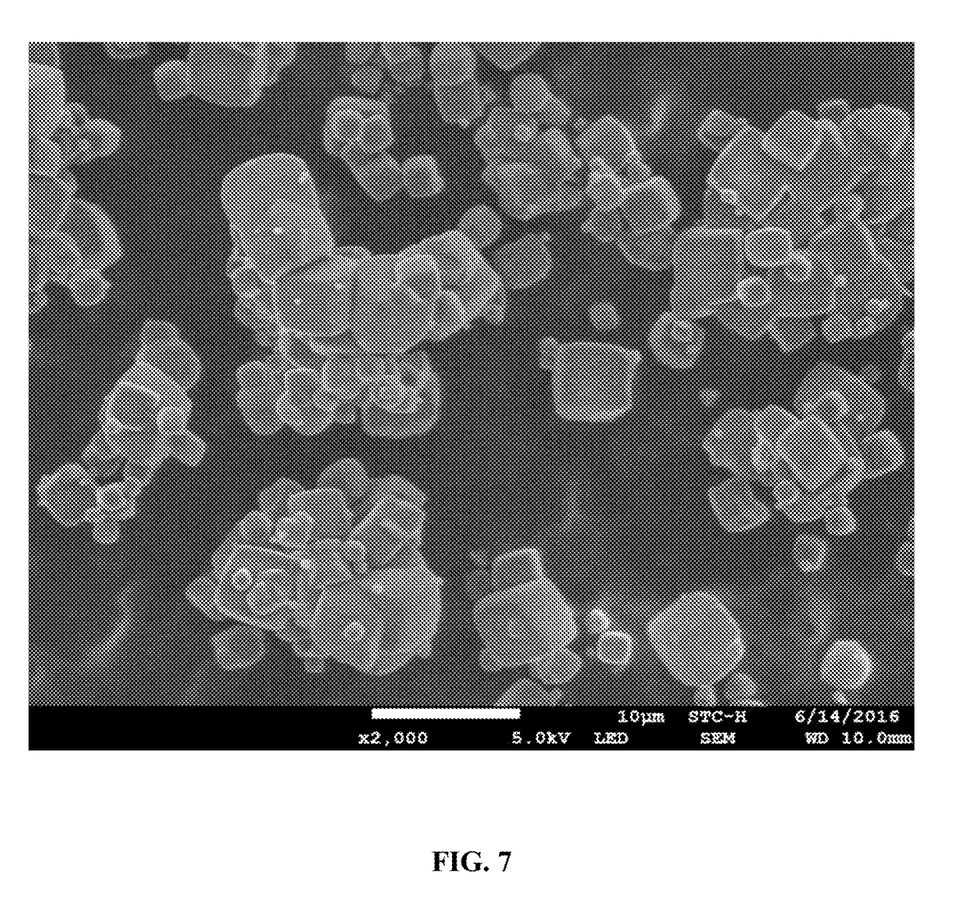

Table 4 shows the theoretical and actual molar ratios for the zeolite with similar concentrations as those from Table 3, with the exception that no PEI was added. The crystallization temperature was 170° C. with a crystallization time of 3 days. As can be seen in FIG. 7, the zeolite possessed good crystal structure, but had an average particle size of about 3,000 nm. This indicates that the addition of PEI is necessary to obtain nano-sized zeolite crystals. Moreover, this indicates that too high a concentration of PEI can prevent the material from forming a zeolite, as seen in FIG. 6 where the concentration of PEI (at 1.5 wt. %) was too high to form a zeolite.

TABLE 4

|  | Si/Al$_2$ ratio | Si | R | H$_2$O | Al$_2$ |
| --- | --- | --- | --- | --- | --- |
| Theoretical | 100:1 | 100 | 80 | 3,500 | 1 |
| Actual | 100:1 | 99.4 | 79.6 | 3,428 | 1 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising," "containing," or "including" various components or steps, the compositions, systems, and methods also can "consist essentially of" or "consist of" the various components and steps.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A catalyst comprising:
   a zeolite, wherein the zeolite has:
      a CHA framework;
      a particle size less than or equal to 80 nanometers obtained by using a crystal growth inhibitor in a concentration in the range of 0.1 to 1 weight percent of a silica precursor and an alumina precursor; and
      a silica to alumina mole ratio in the range of about 50:1 to about 150:1.

2. The catalyst according to claim 1, wherein the zeolite has a particle size less than or equal to 50 nanometers.

3. The catalyst according to claim 1, wherein the zeolite further comprises a metal dopant.

4. The catalyst according to claim 3, wherein the dopant is selected from copper (Cu), nickel (Ni), iron (Fe), zinc (Zn), manganese (Mn), and molybdenum (Mo).

5. The catalyst according to claim 1, wherein the catalyst is synthesized using mole ratios of oxides as follows: (0.5 to 1.0) $R_2O$: (0 to 0.50) $M_2O$—$W_2O_3$: (greater than 5) YO, wherein M is an alkali metal cation, W is selected from the group consisting of aluminum, gallium and mixtures thereof, Y is selected from the group consisting of silicon, germanium and mixtures thereof, and R is a quaternary lower alkylammonium cation compound.

6. The catalyst according to claim 1, wherein the pore diameter of the zeolite ranges from 3 angstroms (Å) to 15 Å.

7. The catalyst according to claim 1, wherein the pore volume of the zeolite is 0.29 milliliters per gram.

8. The catalyst according to claim 1, wherein the catalyst is used to produce olefins.

9. The catalyst according to claim 1, wherein the catalyst is used to produce alkenes with an increased carbon chain.

10. The catalyst according to claim 1, wherein the zeolite further comprises a metal to form a metal zeolite catalyst.

11. The catalyst according to claim 10, wherein the metal is selected from copper, iron, or cobalt.

12. The catalyst according to claim 10, wherein the metal zeolite catalyst is used for selective catalytic reduction (SCR) or $deNO_x$ of nitrogen oxide ($NO_x$).

13. The catalyst according to claim 10, wherein the metal zeolite catalyst is used in a gas to liquid (GTL) reaction.

14. The catalyst according to claim 1, wherein the catalyst has an activity of at least 70% under operating conditions.

15. The catalyst according to claim 1, wherein the catalyst has a selectivity of desired products of at least 60% under operating conditions.

\* \* \* \* \*